United States Patent
Rossen et al.

(10) Patent No.: US 12,318,114 B2
(45) Date of Patent: Jun. 3, 2025

(54) NEEDLE GUIDE FOR ULTRASOUND-GUIDED FREEHAND BIOPSY AND/OR ABLATION NEEDLE INSERTION

(71) Applicant: B-K MEDICAL APS, Herlev (DK)

(72) Inventors: Rasmusen Holdensgaard Rossen, Vanlose (DK); Torben Svanberg Nielsen, Copenhagen (DK)

(73) Assignee: B-K MEDICAL APS, Herlev (DK)

( * ) Notice: Subject to any disclaimer, the term of this patent is extended or adjusted under 35 U.S.C. 154(b) by 232 days.

(21) Appl. No.: 17/919,404

(22) PCT Filed: Apr. 16, 2020

(86) PCT No.: PCT/IB2020/053628
§ 371 (c)(1),
(2) Date: Oct. 17, 2022

(87) PCT Pub. No.: WO2021/209794
PCT Pub. Date: Oct. 21, 2021

(65) Prior Publication Data
US 2023/0149040 A1    May 18, 2023

(51) Int. Cl.
*A61B 17/34* (2006.01)
*A61B 8/00* (2006.01)
(Continued)

(52) U.S. Cl.
CPC ........ *A61B 17/3403* (2013.01); *A61B 8/4488* (2013.01); *A61B 2017/00477* (2013.01);
(Continued)

(58) Field of Classification Search
CPC .............. A61B 17/3403; A61B 8/4488; A61B 2017/00477; A61B 2017/3405;
(Continued)

(56) References Cited

U.S. PATENT DOCUMENTS 4,542,747 A * 9/1985 Zurinski .............. A61B 8/0833
600/461
4,817,616 A * 4/1989 Goldstein ................ A61B 8/12
600/463
(Continued)

FOREIGN PATENT DOCUMENTS

CN   203425000 U   2/2014
JP     0663041 B2   8/1994
(Continued)

OTHER PUBLICATIONS

CN203425000U English Abstract; 1 page; Espacenet search Jul. 2, 2024.
(Continued)

*Primary Examiner* — Bo Joseph Peng
(74) *Attorney, Agent, or Firm* — Daugherty & Del Zoppo, Co. LPA (57) ABSTRACT

An instrument guide (334) is attachable to an ultrasound imaging probe (304) to guide a needle. The instrument guide comprises a length (404), a width (406) and a height (408), a coupler (336) configured to couple the instrument guide to the ultrasound imaging probe, and a single elongate needle guide slot (410) configured to guide placement of the needle for an ultrasound-guided procedure. In another instance, the instrument guide is attached to the probe via a coupler (336). A method includes attaching a needle guide to an ultrasound imaging probe, wherein the needle guide includes a single elongate needle guide slot configured to guide placement of a needle during an ultrasound-guided needle placement procedure, positioning the probe relative to tissue of interest, and placing a needle at the tissue of interest using the needle guide.

17 Claims, 8 Drawing Sheets

(51) Int. Cl.
 *A61B 17/00* (2006.01)
 *A61B 18/14* (2006.01)
(52) U.S. Cl.
 CPC ............... *A61B 2017/3405* (2013.01); *A61B 2018/1425* (2013.01)
(58) Field of Classification Search
 CPC .... A61B 2018/1425; A61B 2017/3413; A61B 8/0841; A61B 8/12
 See application file for complete search history.

(56) References Cited

U.S. PATENT DOCUMENTS

| | | | | |
|---|---|---|---|---|
| 4,838,506 A | * | 6/1989 | Cooper | A61B 8/12 248/200 |
| 4,883,059 A | | 11/1989 | Stedman et al. | |
| 4,899,756 A | * | 2/1990 | Sonek | A61B 8/0841 600/461 |
| 4,911,173 A | * | 3/1990 | Terwilliger | A61B 17/3403 600/101 |
| 6,203,499 B1 | | 3/2001 | Imling et al. | |
| 12,075,989 B2 | * | 9/2024 | Whitmore | A61B 8/12 |
| 2005/0059891 A1 | | 3/2005 | Kosaku | |
| 2007/0282205 A1 | | 12/2007 | Furia | |
| 2012/0095339 A1 | * | 4/2012 | Tashiro | A61B 90/11 600/443 |
| 2022/0240904 A1 | * | 8/2022 | Patel | A61B 10/0241 |

FOREIGN PATENT DOCUMENTS

| | | | |
|---|---|---|---|
| JP | 2005034273 A | 2/2005 | |
| JP | 2006075386 A | 3/2006 | |
| JP | 2007275419 A | 10/2007 | |
| JP | 2012081134 A | 4/2012 | |
| WO | 2000/40155 A1 | 7/2000 | |
| WO | WO-2020181388 A1 * | 9/2020 | ......... A61B 17/3403 |

OTHER PUBLICATIONS

JP application 2022-562694 filed Oct. 13, 2022—Notice of Appeal issued Apr. 3, 2024; 3 pages; Machine Translation.
International Search Report for PCT/IB2020/053628 published as WO20211209794A1 on Oct. 21, 2021.
JP application 2022-562694 filed Oct. 13, 2022—Office Action issued Oct. 18, 2023; Machine Translation; 5 pages.
JP2006075386—English Abstract; Espacenet search; Jan. 18, 2024; 1 page.
JP2007275419—English Abstract; Espacenet search; Jan. 18, 2024; 1 page.
JPH0663041—English Abstract; Espacenet search; Jan. 18, 2024; 1 page.

* cited by examiner

NEEDLE GUIDE FOR ULTRASOUND-GUIDED FREEHAND BIOPSY AND/OR ABLATION NEEDLE INSERTION

RELATED APPLICATION

This application is a national filing of PCT application Serial No. PCT/IB2020/053628, filed Apr. 16, 2020, published as WO20211209794A1 on Oct. 21, 2021.

TECHNICAL FIELD

The following generally relates to ultrasound and more particularly to a needle guide for ultrasound-guided freehand biopsy and/or ablation needle insertion. The following is also amenable for guiding other instruments.

BACKGROUND

Figure 1:
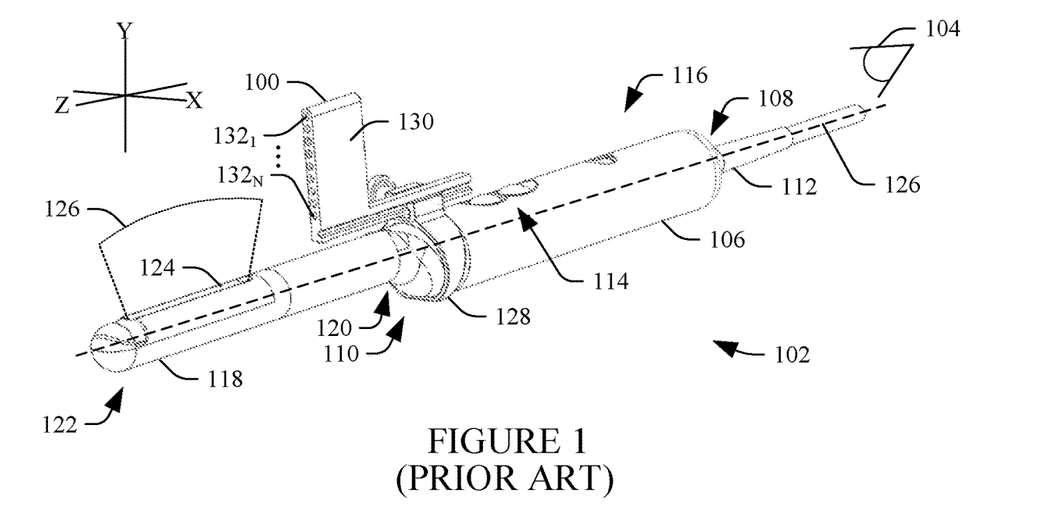
FIG. 1 illustrates an isometric view of a prior art needle guide, which includes a plurality of predetermine individual and distinct static channels with a given spacing therebetween, mounted to an ultrasound probe.
Figure 2:
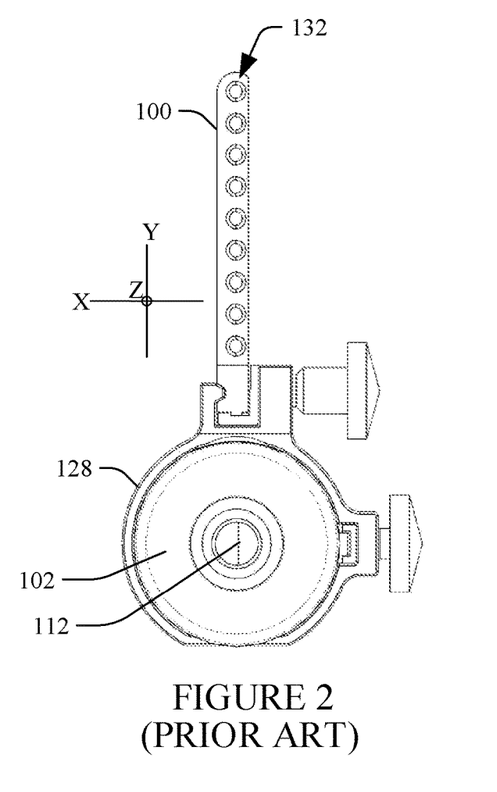
FIG. 2 illustrates a view from a back of the ultrasound probe and the needle guide.

Ultrasound imaging has provided useful information about the interior characteristics of an object or subject under examination. Such imaging has included transrectal ultrasound-guided freehand transperineal biopsy and ablation needle insertion. For such procedures, a needle guide is attached to the ultrasound probed and includes several distinct channels for guiding biopsy or ablation needles. FIG. 1 shows an isometric view of an example prior art needle guide 100 attached to an endorectal probe 102, and FIG. 2 shows a view of the needle guide 100 and the endorectal probe 102 looking from behind 104 the needle guide 100 and the endorectal probe 102.

The probe 102 includes a handle 106 with a first end 108 and a second end 110, which opposes the first end 108 (i.e. a second opposing end 110). The probe 102 further a cable 112 for transferring signals and/or data to and from the probe 102 that is located at the first end. The probe 102 further includes controls 114 located on a top side 116 of the handle 104 between the first and second opposing ends 108 and 110. The probe 102 further includes an elongate tubular shaft 118 with a first end 120 and a second end 122, which opposes the first end 120 (i.e. a second opposing end 122). The first end 120 of the elongate tubular shaft 118 is coupled to the second opposing end 110 of the handle 106.

The probe 102 further includes an acoustic window 124 disposed at the second opposing end 122 of the elongate tubular shaft 112 118. The acoustic window extends partially down a long axis 126 of the probe 102 towards the first end 120 of the elongate tubular shaft 118. The probe 102 further include a transducer array (not visible) that is housed inside of the elongate tubular shaft 118 under the acoustic window 124 and that is configured to generate an image plane 126. The long axis 126 extends along a Z-axis, wherein an X-Y plane represents the axial plane, a Z-Y plane represents the sagittal plane, and an X-Z plane represents the coronal plane.

The needle guide 100 includes a clamp 128 configured to releasably attach the needle guide 100 to the probe 102. The needle guide 100 further includes a member 130 that extends away from the clamp 128 in the positive Y-axis direction. The member 130 includes a series of individual distinct channels $132_1, \ldots, 132_N$, where N is a positive integer (collectively referred to herein as channels 132). The individual distinct channels 132 are statically positioned, one on top of each other in the positive Y-axis direction, with a predetermined spacing therebetween (e.g., five millimeters, 5 mm).

With the needle guide 100, a clinician is restricted to the paths defined by the static location of the individual distinct channels 132. Unfortunately, the clinician may encounter an obstruction (e.g., the pubic arch bone or a calcification) that blocks one or more of the biopsy needle paths to tissue of interest (e.g., a certain part of the prostate) through a channel 132. In such a circumstance, the clinician may have to remove the needle guide 100 and rely on experience to freely move and/or angle the needle without the needle guide 100. As a consequence, anatomy such as a blood vessel, the urinary tract, etc., may be accidentally punctured during a biopsy, which may result in harm to a patient.

Additionally, the clinician may end up moving and/or rotating the ultrasound probe, e.g., to reposition the needle paths to avoid obstructions. However, this may result in deformation of tissue (e.g., the prostate in a prostate examination) from physical contact with and force from the ultrasound probe, which may compromise fusion of any ultrasound images acquired during the examination with pre-procedure images such as magnetic resonance (MR) and/or computed tomography (CT) images, where, due to the deformation, the tissue in the ultrasound images may not align as well with the structure in the pre-procedure images Ablation needle insertion may also encounter such obstructions that block the ablation needle paths through the channels 142. In addition, with ablation needle insertion, the needle guide 100 will not be able to be removed after ablation needle insertion with ablation needles that have protruding geometry at the back because the protruding geometry will not slide through the channels 142. If the clinician wants to perform the ablation procedure without the needle guide 100 in the way, the clinician would have to place the ablation needles without the needle guide 100 and rely on experience to carefully insert the ablation needles.

In view of the foregoing, there is a need for an improved needle guide at least for ultrasound-guided freehand transperineal biopsy and/or transrectal ablation needle insertion.

SUMMARY

Aspects of the application address the above matters, and others.

In one aspect, a system includes an instrument guide with a length, a width and height, a coupler configured to couple the instrument guide to the ultrasound imaging probe, and a single elongate needle guide slot configured to guide placement of the needle for an ultrasound-guided procedure.

In another aspect, a system includes an ultrasound imaging probe with a transducer array including elements configured to generate an image plane in a sagittal plane of the probe, thereby generating a sagittal image plane. The system further includes an instrument guide with a length, a width and height, a coupler configured to couple the instrument guide to the ultrasound imaging probe, and a single elongate needle guide slot configured to guide placement of the needle for an ultrasound-guided procedure.

In yet another aspect, a method includes attaching a needle guide to an ultrasound imaging probe, wherein the needle guide includes a single elongate needle guide slot configured to guide placement of a needle during an ultrasound-guided needle placement procedure. The method further includes positioning the probe relative to tissue of interest. The method further includes placing a needle at the tissue of interest using the needle guide.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which.

DETAILED DESCRIPTION

Figure 3:
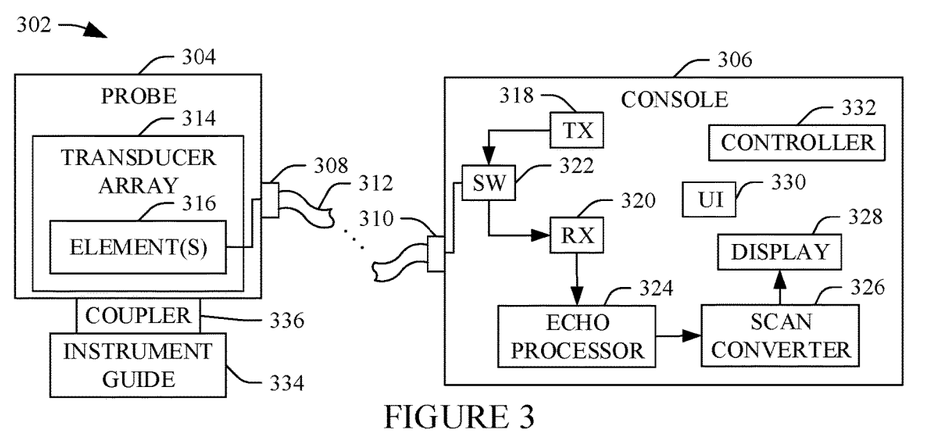
FIG. 3 diagrammatically illustrates a system including an ultrasound console, an ultrasound probe, an instrument guide and a coupler, in accordance with an embodiment herein.

FIG. 3 illustrates an example imaging system 302 such as an ultrasound imaging system/scanner. The imaging system 302 includes a probe 304 and a console 306, which interface with each other through suitable complementary hardware (e.g., cable connectors 308 and 310 and a cable 312 as shown, etc.) and/or wireless interfaces (not visible).

The probe 304 includes a transducer array 314 with one or more transducer elements 316. The one or more transducer elements 316 are arranged as a 1-D or 2-D, linear, curved and/or otherwise shaped, fully populated or sparse, etc. array. The elements 316 are configured to convert excitation electrical pulses into an ultrasound pressure field and convert a reflected and received ultrasound pressure field (an echo) into electrical (e.g., a radio frequency (RF)) an echo signal. The probe 304 is configured for at least transperineal and/or transrectal ultrasound-guided procedures. An example of such a probe is the probe 102 of FIG. 1. Other probes are also contemplated herein.

The console 306 includes transmit circuitry (TX) 318 configured to generate the excitation electrical pulses and receive circuitry (RX) 320 configured to process the RF signals, e.g., amplify, digitize, and/or otherwise process the RF signals. The console 306 further includes a switch (SW) 322 configured to switch between the TX 318 and RX 320 for transmit and receive operations, e.g., by electrically connecting and electrically disconnecting the TX 318 and the RX 320. In an alternative embodiment, the TX 318 and the RX 320 are each connected to their own switches.

The console 306 includes further an echo processor 324 configured to process the signal from the RX 320. For example, in one instance the echo processor 324 is configured to beamform (e.g., delay-and-sum) the signal to construct a scanplane of scanlines of data. The echo processor 324 can process data from 1-D and/or 2-D probes for 2-D, 3-D and/or 4-D applications. The echo processor 324 can be implemented by a hardware processor such as a central processing unit (CPU), a graphics processing unit (GPU), a microprocessor, etc.

The console 306 further includes a scan converter 326 configured to scan convert the output of the echo processor 324 to the coordinate system of a display 328, which display the scan converted data as images. In one instance, the scan converting includes changing the vertical and/or horizontal scan frequency of signal based on the display 328. The scan converter 326 can be configured to employ analog scan converting techniques and/or digital scan converting techniques. In one instance, the image are images of the sagittal plane.

The console 306 further includes a user interface 330, which includes one or more input devices (e.g., a button, a touch pad, a touch screen, etc.) and one or more output devices (e.g., a display screen, a speaker, etc.). The console 306 further includes a controller 332 configured to control one or more of the probe 304, the transmit circuitry 318, the receive circuitry 320, the switch 322, the echo processor 324, the scan converter 326, the display 328, the user interface 330, and/or one or more other components of the imaging system 302.

In the illustrated embodiment, the imaging system 302 is used in connection with an instrument holder 334 such as a needle guide, e.g., for guiding a biopsy needle, an ablation needle, etc. As such, in one instance, the instrument holder 334 is used to guide a biopsy needle to a target region within an object or subject. In another instance, the instrument holder 334 is used to guide an ablation needle to a target region within an object or subject. A coupler 336 couples the instrument holder 334 and the probe 304. An example of the coupler 136 is the clamp of FIGS. 1 and 2. Other known couplers for attaching a needle guide to a probe are contemplated herein.

As described in greater detail below, in one instance the instrument holder 334 allows a biopsy needle and/or an ablation needle to be moved freely within the ultrasound sagittal image plane (in-plane), while limiting out-of-plane movement. In one instance, this is achieved by utilizing a closed elongated slot as a guiding feature. Such a slot mitigates the shortcoming of encountering an obstruction (e.g., pubic arch bone or a calcification) in the path of a channel of a needle guide with static channel locations with predetermined spacing or having to insert the needle without any needle guide and potentially puncturing tissue and causing harm.

Also described in greater detail below, in another embodiment, the instrument holder 334 is configured so that it can be removed from the probe 304 after ablation needle placement for the ablation procedure. In one instance, this is achieved through a configuration in which the elongated slot is configured to be a closed slot during placement and then opened after placement so that the instrument holder 334 can be removed while the ablation needle remains in place. This additionally mitigates having to perform the ablation with the procedure instrument holder 334 in place or perform needle placement freehand without the instrument holder 334 and/or add multiple ablation needles with a freehand guide.

Figure 4:
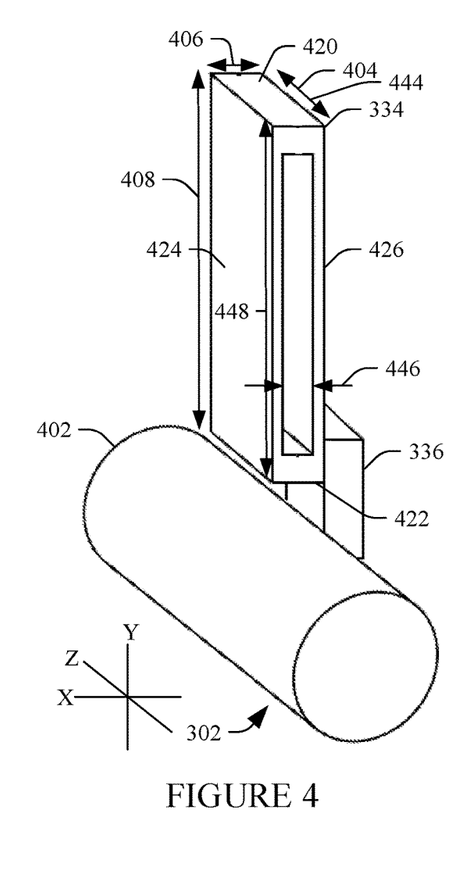
FIG. 4 diagrammatically illustrates the instrument guide showing an elongate needle guide slot therein, in accordance with an embodiment herein.
Figure 5:
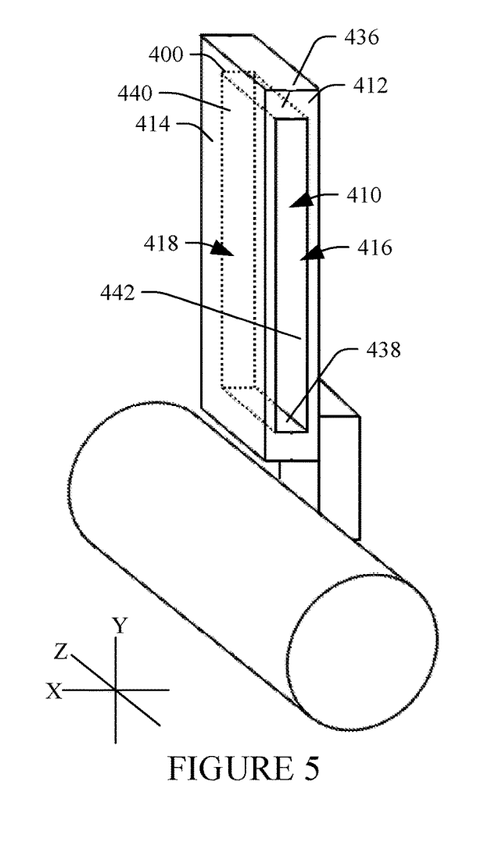
FIG. 5 diagrammatically illustrates the instrument guide of FIG. 4 showing internal walls of the elongate needle guide slot, in accordance with an embodiment herein.

FIGS. 4 and 5 illustrate an isometric view of a non-limiting example of the instrument holder 334 coupled to a sub-portion 402 of the probe 304 via the coupler 336. Again, an example of the probe 304 includes the probe 102 of FIGS. 1 and 2. In this embodiment, the sub-portion 402 corresponds to part of the handle 104 in FIG. 1. FIGS. 4 and 5 are identical except that FIG. 5 includes additional dotted lines 400 to show lines of interior walls that are not all visible from the outside from the illustrated viewpoint of FIG. 4. For clarity, each reference number will only be shown in one of FIG. 4 or 5 and not both.

In this example, the instrument holder 334 is rectangular prism shaped, with a length 404 in a range of 5 to 50 mm, a width 406 in a range from greater than 0.7176 to greater than 2.108 mm (e.g., 0.75 to 2.2 mm) X to Y mm, and a height 408 in a range of 3 to 65 mm A single elongated slot 410 extends entirely through the width 406 from a first side 412 to a second side 414, creating openings 416 and 418 at each side. The single elongated slot 410 is entirely enclosed by sides 420, 422, 424 and 426 respectively by interior walls 436, 438, 440 and 442. In this embodiment, the single elongated slot 410 is also rectangular prism shaped. Other shapes of the instrument holder 334 and/or the single elongated slot 410 (including an arc shaped, rounded, curved, irregular, etc. side(s)), lengths 404, widths 406, heights 408, etc. are contemplated herein. In this embodiment, there are no other slots.

Figure 6:
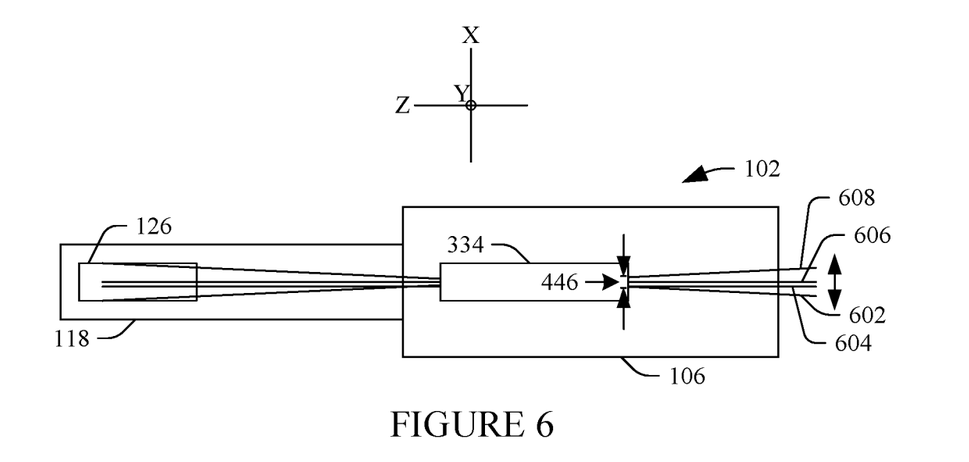
FIG. 6 diagrammatically illustrates needle paths from a top down view of the instrument guide and probe of FIGS. 4 and 5, in accordance with an embodiment herein.
Figure 7:
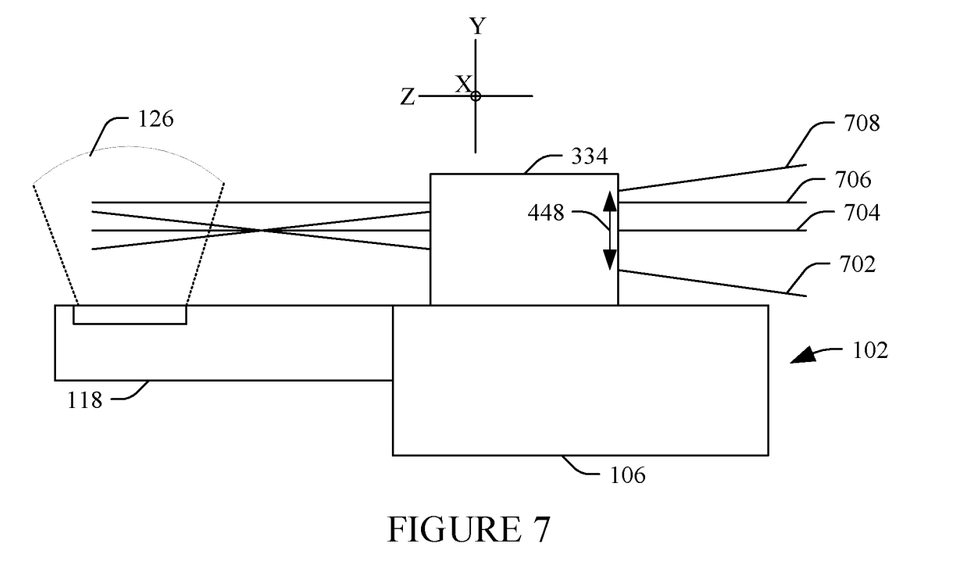
FIG. 7 diagrammatically illustrates needle paths from a side view of the instrument guide and probe of FIGS. 4 and 5, in accordance with an embodiment herein.

A length 444 of the slot 410 is the same as the length 404 since the slot 410 extends entirely through the width 406. A width 446 of the slot 410 is in a range from 0.7176 to 2.108 mm (e.g., to accommodate 22-14 gauge needles). A height 448 of the slot 410 is in a range from fifty (50) to seventy (70) mm. The length 444, the width 446 and the height 448 are such that a biopsy and/or an ablation needle can be passed from the first side 412 to the second side 414 and freely moved in-plane, while being prohibited from being moved out-of-plane. FIG. 6 shows the guide 100 limits paths 602, 604, 606 and 608 along the width 446 from the top 116 of the probe 102, and FIG. 7 shows free hand paths 702, 704, 706 and 708 along the height 448 from a side of the probe 102.

Figure 8:
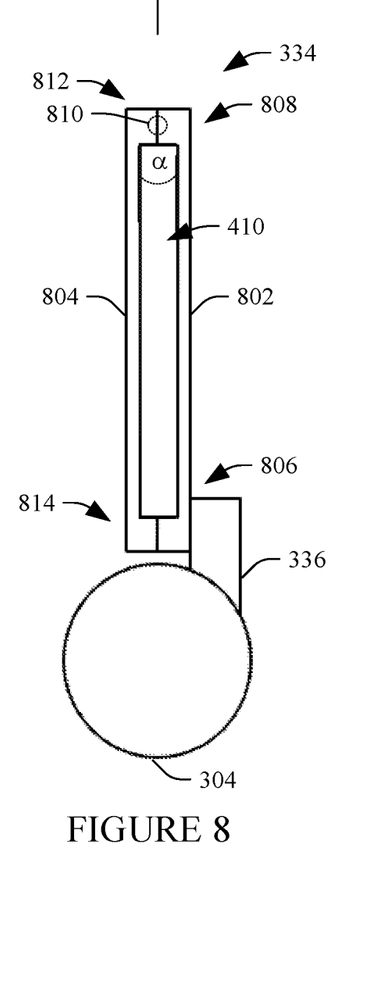
FIG. 8 diagrammatically illustrates a variation of the instrument guide with first and second legs together, in accordance with an embodiment herein.
Figure 9:
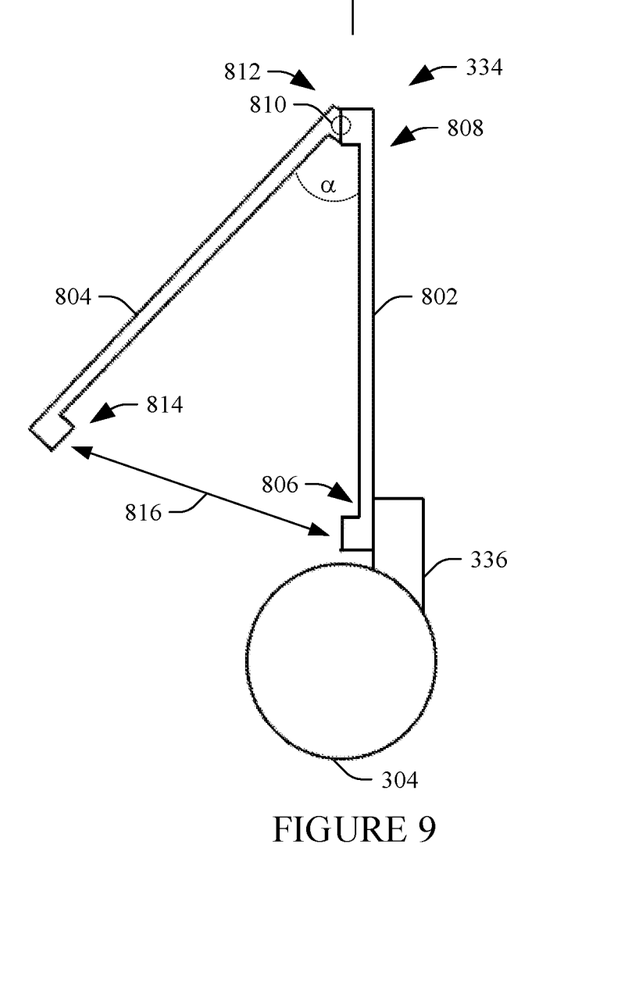
FIG. 9 diagrammatically illustrates the variation in FIG. 8 with the first and second legs separated, in accordance with an embodiment herein.

FIGS. 8 and 9 diagrammatically illustrates a variation of the instrument holder 334 from the back 104. With this variation, the instrument holder 334 includes a first leg 802 and a second leg 804. A first end 806 of the first leg 802 is coupled to the coupler 336. A second, opposing end 808 of the first let 802 is coupled to a bearing 810. A first end 812 of the second leg 804 is also coupled to the bearing 810. A second, opposing end 814 of the second leg 804 is not coupled to any component. The bearing 810 is configured to allow the first and second legs 802 and 804 to rotate relative to each other in the X-Y plane.

FIG. 8 shows the first leg 802 rotated towards the second leg 802 such that the second, opposing end 814 of the second leg 804 is in physical contact with the first end 806 of the first leg 802, creating the closed slot 410. In this position, an angle α between the second, opposing end 814 of the second leg 804 and the first end 806 of the first leg 802 is zero (0). FIG. 9 shows the first leg 802 rotated approximately forty-five degrees (45°) away from the second legs 802 such that the second, opposing end 814 of the second leg 804 is separated from the first end 806 of the first leg 802 by a non-zero distance 816.

Although FIGS. 8 and 9 show a rotation of approximately 45°, in other embodiments the maximum rotation can be more or less. For example, in one instance the maximum rotation is less than 45°. In another instance, the maximum rotation is 90°. In another instance, the maximum rotation is 180°. In another instance, the maximum rotation is 270°. In another instance, the maximum rotation is greater than 270°, e.g., such that the second, opposing end 814 of the second leg 804 is in physical contact with the first end 806 of the first leg 802 or the coupler 336.

The rotation, in general, is such that after placement of an ablation needle(s) using the instrument guide 334, the second, opposing end 814 of the second leg 804 can be rotated enough such that the distance 816 provide a gap that allows the instrument guide 334 to be removed, while leaving the ablation needle(s) in place so that the ablation needle(s) can be used to perform an ablation procedure. A non-limiting example of the bearing 810 is a hinge. Examples of suitable hinges include a spring hinge, a barrel hinge, a pivot hinge, and/or other hinges that allow such rotation.

Figure 10:
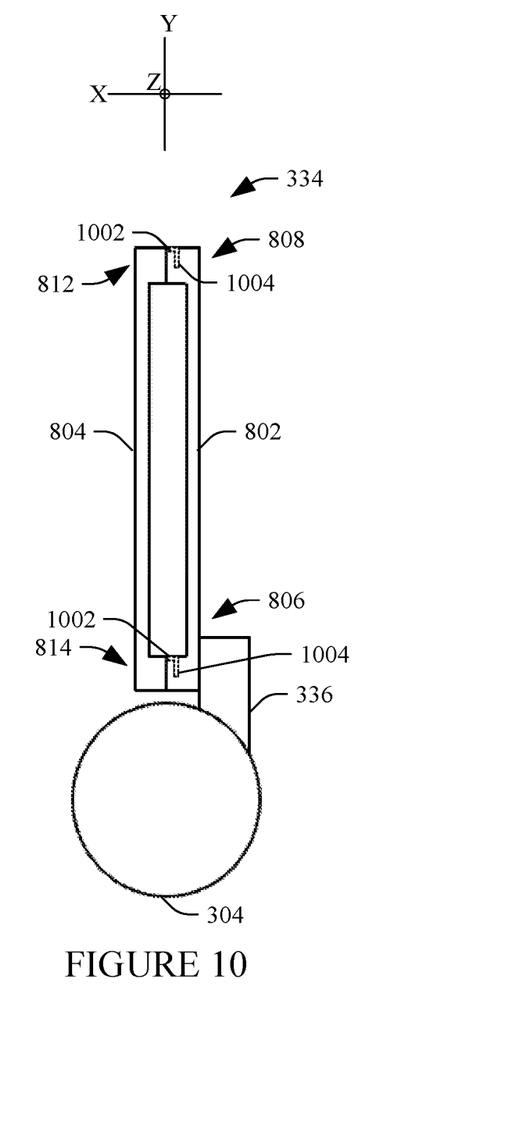
FIG. 10 diagrammatically illustrates another variation of the instrument guide with the first and second legs together, in accordance with an embodiment herein.
Figure 11:
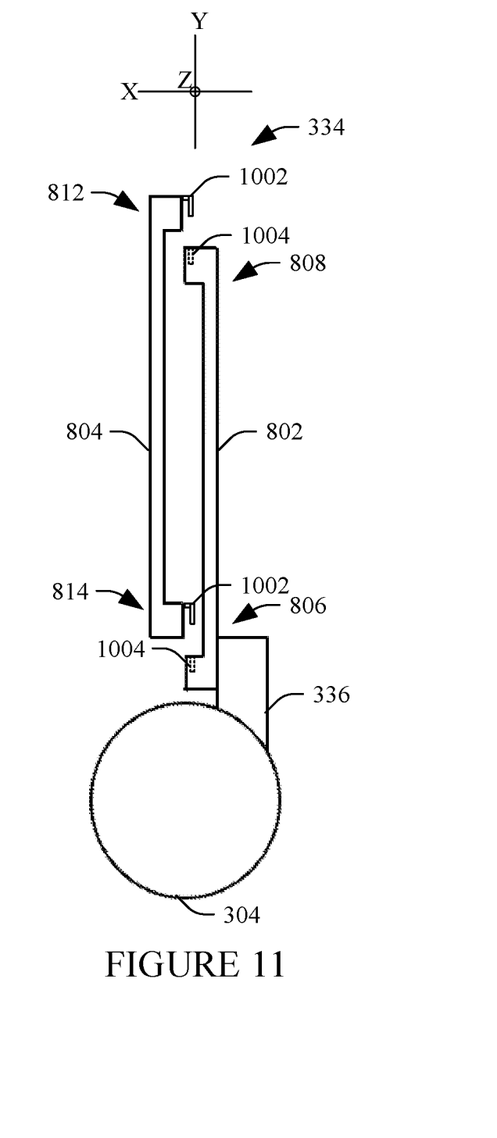
FIG. 11 diagrammatically illustrates the variation in FIG. 10 with the first and second legs separated, in accordance with an embodiment herein.

FIGS. 10 and 11 diagrammatically illustrates another variation of the instrument holder 334 from the back 104. With this variation, the ends 812 ends 814 of the second leg 804 includes protrusions 1002, and the ends 808 and 814 of the first let 802 include recesses 1004. Each protrusion 1002 is configured to slide into and out of one of the recesses 1004. When slid into the recesses 1004, the protrusions 1002 engage the second leg 802 and holds the first and second legs 802 and 804 together. When slid out of the recesses 1004, the protrusions 1002 disengage the second leg 802 and the second leg 804 can be moved away from the first leg.

Similarly, this allows the instrument guide 334 to be removed after ablation needle(s) placement, while leaving the ablation needle(s) so that the ablation needle(s) can be used to perform an ablation procedure. Other configurations of the protrusion and recess are contemplated herein. In addition, FIGS. 10 and 11 show two sets or pairs of protrusions and recesses 1002 and 1004. In another embodiment, the instrument guide 334 includes only a single pair of the protrusion and recess 1002 and 1004. In another embodiment, the instrument guide 334 includes more than two pairs of protrusions and recesses 1002 and 1004.

Figure 12:
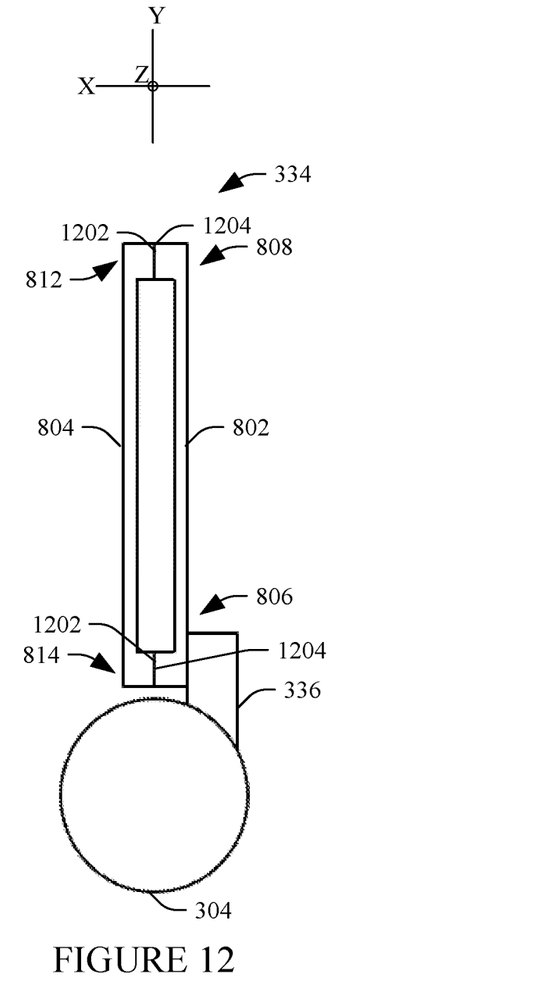
FIG. 12 diagrammatically illustrates still another variation of the instrument guide with the first and second legs together, in accordance with an embodiment herein.
Figure 13:
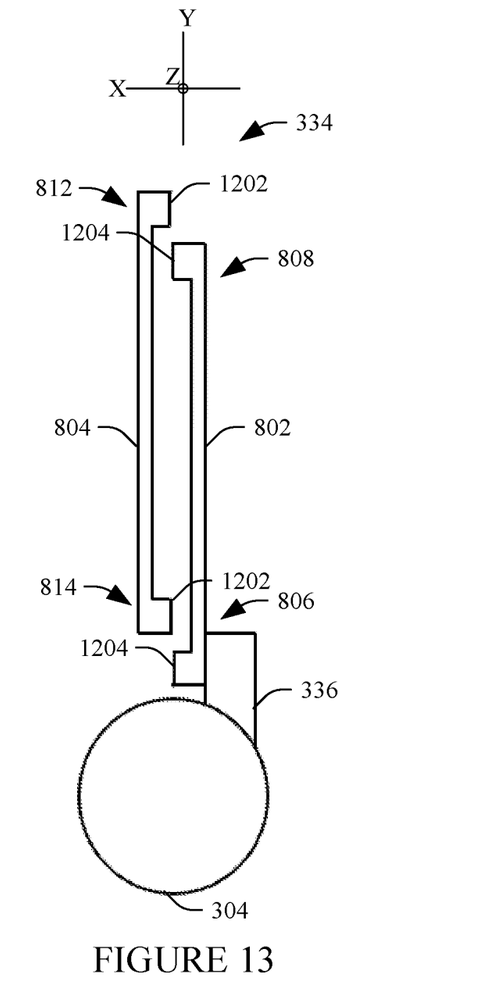
FIG. 13 diagrammatically illustrates the variation in FIG. 12 with the first and second legs separated, in accordance with an embodiment herein.

FIGS. 12 and 13 diagrammatically illustrates another variation of the instrument holder 334 from the back end 104. With this variation, the ends 806 and 808 and the ends include 812 ends 814 respectively include complementary fasteners 1202 and 1204 that engage when mated together and disengage with pulled apart. Examples of suitable fasteners includes hook-and-loop, hook-and-pile, touch and/or other fasteners. One particular fastener is a VELCRO® Brand fastener, which is a product of Velcro Companies, headquartered in Manchester, NH, USA. Other fasteners are also contemplated herein.

Similarly, separating the complementary fasteners 1202 and 1204 allows the instrument guide 334 to be removed after ablation needle(s) placement, while leaving the ablation needle(s) so that the ablation needle(s) can be used to perform an ablation procedure. Other configurations are contemplated herein. In addition, FIGS. 12 and 13 show two sets or pairs of fasteners 1202 and 1204. In another embodiment, the instrument guide 334 includes only a single pair of the fasteners 1202 and 1204. In another embodiment, the instrument guide 334 includes more than two pairs of the fasteners 1202 and 1204.

Figures 14, 15:
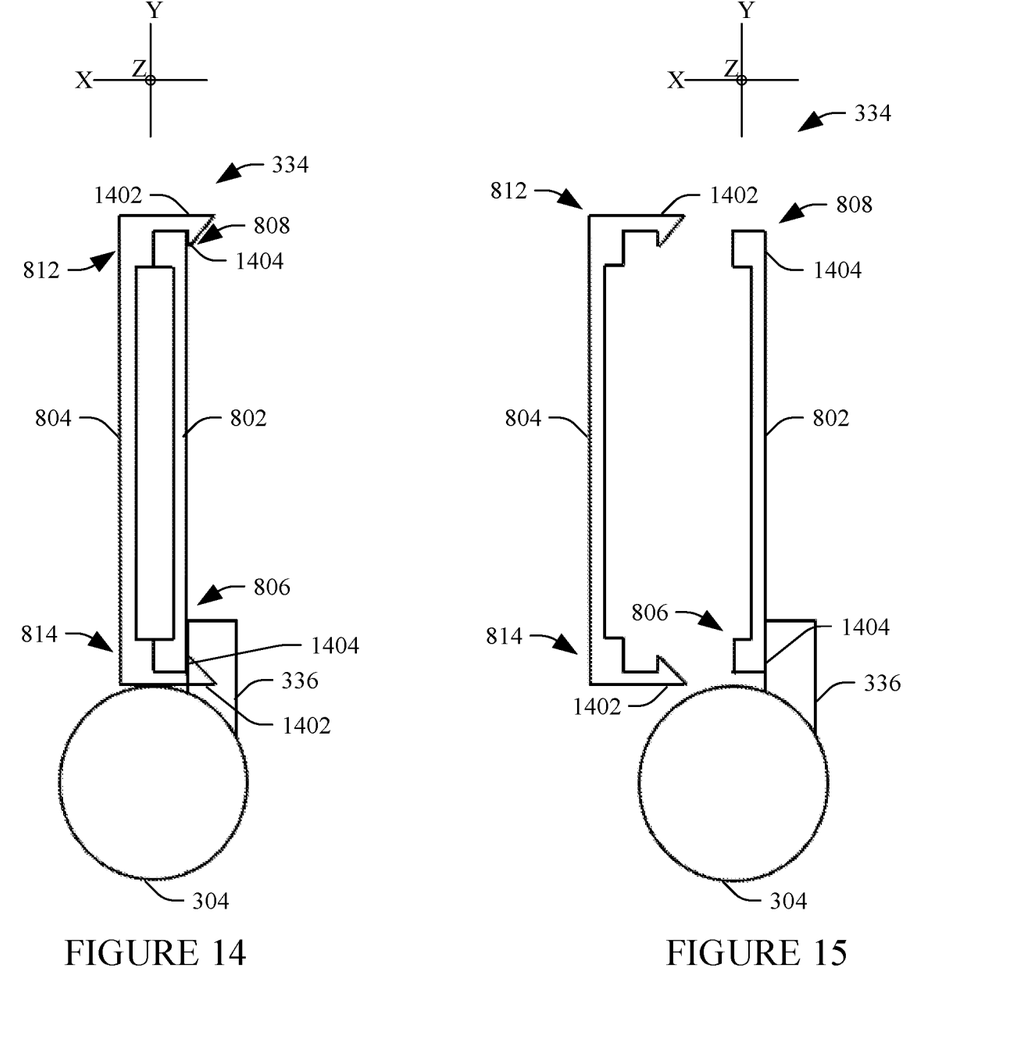
FIG. 14 diagrammatically illustrates yet another variation of the instrument guide with the first and second legs together, in accordance with an embodiment herein.
FIG. 15 diagrammatically illustrates the variation in FIG. 14 with the first and second legs separated, in accordance with an embodiment herein.

FIGS. 14 and 15 diagrammatically illustrates another variation of the instrument holder 334 from the back end 104. With this variation, the ends 812 ends 814 of the second leg 804 includes hooks 1402. Each of the hooks 1402 is respectively configured to wrap around and snap onto the first and second ends 806 and 808 of the first leg 802, which engages the hooks 1402 with a back side 1404 of the first leg 802. When snapped on, the hooks 1402 engage the second leg 802 and holds the first and second legs 802 and 804 together. When released, the hooks 1402 disengage the second leg 802 and the second leg 804 can be moved away from the first leg 802.

Similarly, this allows the instrument guide 334 to be removed after ablation needle(s) placement, while leaving the ablation needle(s) so that the ablation needle(s) can be used to perform an ablation procedure. Other configurations of the hooks 1402 are contemplated herein. In addition, FIGS. 14 and 15 show two sets hooks 1402. In another embodiment, the instrument guide 334 includes only a hook 1402. In another embodiment, the instrument guide 334 includes more than two hooks 1402.

Figure 16:
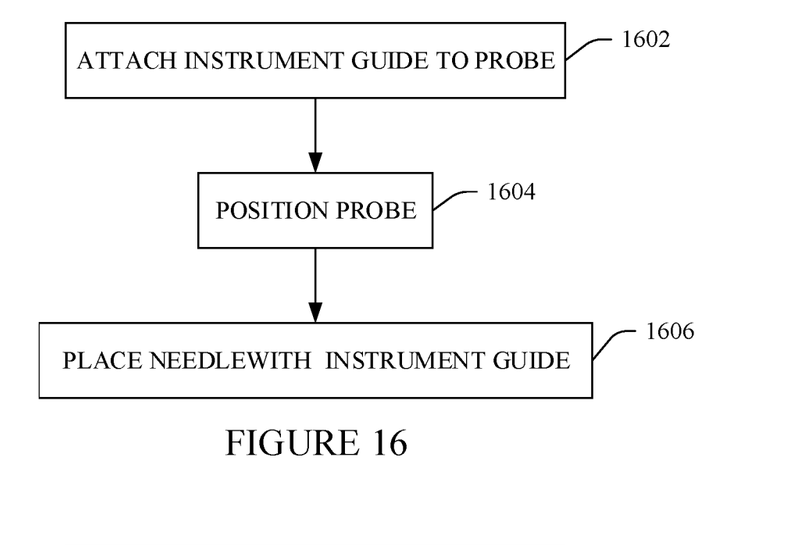
FIG. 16 illustrates a method, in accordance with an embodiment herein.

FIG. 16 illustrates an example method in accordance with an embodiment herein.

At 1602, the instrument guide 334 is attached to the probe 304, as described herein and/or otherwise.

At 1604, the probe 304 is positioned to image tissue of interest.

At 1606, the instrument guide 334 is used to place an instrument at the tissue of interest, as described herein and/or otherwise.

The instrument is then used to perform a procedure. The probe 303 can be removed once the procedure is completed.

Figure 17:
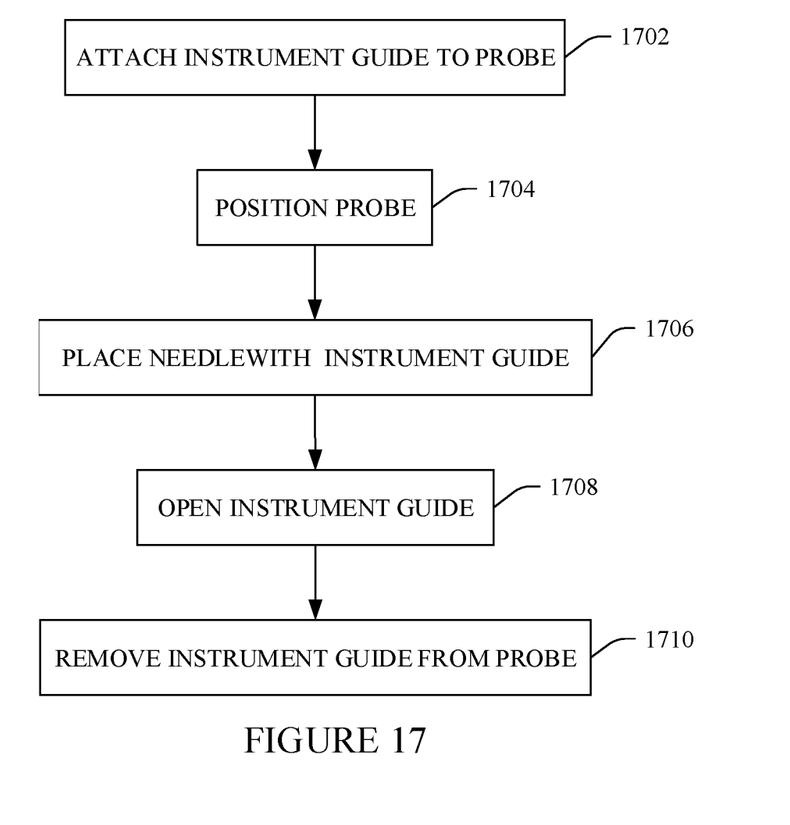
FIG. 17 illustrates another method, in accordance with an embodiment herein.

FIG. 17 illustrates an example method in accordance with an embodiment herein.

At 1702, the instrument guide 334 is attached to the probe 304, as described herein and/or otherwise.

At 1704, the probe 304 is positioned to image tissue of interest.

At 1706, the instrument guide 334 is used to place at least one ablation needle in the tissue of interest.

At 1708, the first and second legs 802 and 804 of the instrument guide 334 are separated, as described herein and/or otherwise.

At 1710, at least the instrument guide 334 is removed, as described herein and/or otherwise.

The ablation procedure is then performed with the at least one ablation needle. The probe 303 can be removed once the procedure is completed.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An instrument guide attachable to an ultrasound imaging probe to guide a needle, the instrument guide, comprising:
   a length, a width and a height;
   a coupler configured to couple the instrument guide to the ultrasound imaging probe;
   a single elongate needle guide slot configured to guide placement of the needle for an ultrasound-guided procedure;
   a first leg, including:
      a first end coupled to the coupler; and
      a second, opposing end;
   a second leg, including:
      a first end; and
      a second, opposing end; and
   a bearing that couples the second, opposing end of the first leg to the first end of the second leg,
   wherein the bearing is configured to allow the first and second legs to rotate relative to each other in an X-Y plane between a first position in which the first end of the first leg physically contacts the second, opposing end of the second leg and at least one other position in which the first end of the first leg is separated from the second, opposing end of the second leg by a non-zero distance.

2. The instrument guide of claim 1, wherein the single elongate slot is enclosed by sides that allows free in-plane movement of the needle within the height.

3. The instrument guide of claim 2, wherein the sides of the single elongate slot limit out-of-plane movement of the needle within the width.

4. The instrument guide of claim 1, wherein the instrument guide includes:
   opposing interior walls along the height with a non-zero gap therebetween;
   opposing interior walls along the length with a non-zero gap therebetween; and
   no walls along the width,
   wherein the opposing interior walls along the height and the width provide the single elongate needle guide slot.

5. The instrument guide of any of claim 1, further comprising:
   an ultrasound imaging probe, including:
      a transducer array, including:
         elements configured to generate an image plane in a sagittal plane of the probe.

6. An instrument guide attachable to an ultrasound imaging probe to guide a needle, the instrument guide, comprising:
   a length, a width and a height;
   a coupler configured to couple the instrument guide to the ultrasound imaging probe;
   a single elongate needle guide slot configured to guide placement of the needle for an ultrasound-guided procedure;
   a first leg, including:
      a first end coupled to the coupler; and
      a second, opposing end with a recess; and
   a second leg, including:

a first end with a protrusion; and
a second, opposing end;
wherein the recess is configured to receive the protrusion, the first and second legs are held together when the protrusion is in the recess, and the first and second legs are separable when the protrusion is not in the recess.

7. The instrument guide of claim 6, wherein the single elongate slot is enclosed by sides that allow free in-plane movement of the needle within the height.

8. The instrument guide of claim 7, wherein the sides of the single elongate slot limit out-of-plane movement of the needle within the width.

9. The instrument guide of claim 6, wherein the instrument guide includes:
opposing interior walls along the height with a non-zero gap therebetween;
opposing interior walls along the length with a non-zero gap therebetween; and
no walls along the width,
wherein the opposing interior walls along the height and the width provide the single elongate needle guide slot.

10. An instrument guide attachable to an ultrasound imaging probe to guide a needle, the instrument guide, comprising:
a length, a width and a height;
a coupler configured to couple the instrument guide to the ultrasound imaging probe;
a single elongate needle guide slot configured to guide placement of the needle for an ultrasound-guided procedure;
a first leg, including:
a first end coupled to the coupler; and
a second, opposing end with a fastener; and
a second leg, including:
a first end with a complementary fastener; and
a second, opposing end;
wherein the first and second legs are held together when the fastener and the complementary fastener are engaged, and the first and second legs are separable when the fastener and the complementary fastener are not engaged.

11. The instrument guide of claim 10, wherein the single elongate slot is enclosed by sides that allow free in-plane movement of the needle within the height.

12. The instrument guide of claim 11, wherein the sides of the single elongate slot limit out-of-plane movement of the needle within the width.

13. The instrument guide of claim 10, wherein the instrument guide includes:
opposing interior walls along the height with a non-zero gap therebetween;
opposing interior walls along the length with a non-zero gap therebetween; and
no walls along the width,
wherein the opposing interior walls along the height and the width provide the single elongate needle guide slot.

14. An instrument guide attachable to an ultrasound imaging probe to guide a needle, the instrument guide, comprising:
a length, a width and a height;
a coupler configured to couple the instrument guide to the ultrasound imaging probe;
a single elongate needle guide slot configured to guide placement of the needle for an ultrasound-guided procedure;
a first leg, including:
a first end coupled to the coupler; and
a second, opposing end with a hook; and
a second leg, including:
a first end; and
a second, opposing end;
wherein the first and second legs are held together when the hook is snapped onto a back of the second, opposing end, and the first and second legs are separable when the hook is not snapped onto the back of the second, opposing end.

15. The instrument guide of claim 14, wherein the single elongate slot is enclosed by sides that allow free in-plane movement of the needle within the height.

16. The instrument guide of claim 15, wherein the sides of the single elongate slot limit out-of-plane movement of the needle within the width.

17. The instrument guide of claim 14, wherein the instrument guide includes:
opposing interior walls along the height with a non-zero gap therebetween;
opposing interior walls along the length with a non-zero gap therebetween; and
no walls along the width,
wherein the opposing interior walls along the height and the width provide the single elongate needle guide slot.

* * * * *